[12] United States Patent
Tao et al.

(10) Patent No.: US 10,823,728 B2
(45) Date of Patent: Nov. 3, 2020

(54) INTEGRATED MICROARRAY PRINTING AND DETECTION SYSTEM FOR MOLECULAR BINDING ANALYSIS

(71) Applicants: Nongjian Tao, Fountain Hills, AZ (US); Shaopeng Wang, Chandler, AZ (US)

(72) Inventors: Nongjian Tao, Fountain Hills, AZ (US); Shaopeng Wang, Chandler, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 372 days.

(21) Appl. No.: 15/204,738

(22) Filed: Jul. 7, 2016

(65) Prior Publication Data
US 2017/0038380 A1 Feb. 9, 2017

Related U.S. Application Data

(60) Provisional application No. 62/190,109, filed on Jul. 8, 2015.

(51) Int. Cl.
| | |
|---|---|
| *G01N 21/00* | (2006.01) |
| *G01N 33/557* | (2006.01) |
| *G01N 21/552* | (2014.01) |
| *G01N 33/543* | (2006.01) |

(52) U.S. Cl.
CPC ......... *G01N 33/557* (2013.01); *G01N 21/553* (2013.01); *G01N 33/543* (2013.01); *G01N 2201/122* (2013.01)

(58) Field of Classification Search
CPC ..... G01N 21/554; G01N 21/553; G01N 21/63

USPC ............................................ 422/82.05, 82.09
See application file for complete search history.

(56) References Cited

U.S. PATENT DOCUMENTS

2010/0167946 A1 * 7/2010 Shaw .................... B82Y 15/00
506/9

OTHER PUBLICATIONS

Tyson et al., Sniffers, buzzers, toggles and blinkers: dynamics of regulatory and signaling pathways in the cell., Current Opinion in Cell Biology, Apr. 2003, 15(2):221-31.
(Continued)

*Primary Examiner* — Natalia Levkovich
(74) *Attorney, Agent, or Firm* — George A. Leone; Citadel Patent Law

(57) ABSTRACT

A method and system for analysis of protein interaction kinetics in microarray or whole-cell based formats includes positioning a sensor chip on a prism. The sensor chip is spotted with a plurality of target molecules. A movable printer head deposits a plurality of analyte droplets on predefined regions of the sensor chip surface. A light source transmits light through the prism to excite surface plasmon resonance on the sensor chip surface, whereby the plurality of target molecules bound to the upper surface are changing the SPR resonance angle and therefore the intensity of the reflected beam. A detector receives reflected light transmitted through the prism from the bottom surface. Signals from the detector are received and processed into kinetic data and microarray labeled data to determine molecular interactions and binding kinetic properties for the plurality of analyte droplets.

4 Claims, 11 Drawing Sheets

(56) References Cited

OTHER PUBLICATIONS

Homola et al., Surface plasmon resonance sensors for detection of chemical and biological species., Chemical Reviews, Feb. 2008, 108(2):462-93.

Zhu et al., Functional protein microarray as molecular decathlete: A versatile player in clinical proteomics., Proteomics—Clinical Applications, Dec. 2012, 6(11-12):548-62.

Hu et al., Functional protein microarray technology., Wiley Interdisciplinary Reviews: Systems Biology and Medicine, May 2011, 3(3):255-68.

Zhao et al., Protein biomarkers in cancer: Natural glycoprotein microarray approaches., Current Opinion in Molecular Therapeutics, Dec. 2008, 10(6):602-10.

Hobler and Uhlen, Human protein atlas and the use of microarray technologies., Current Opinion in Biotechnology, Feb. 2008, 19(1):30-5.

Tao et al., Applications of protein microarray technology., Combinatorial Chemistry and High Throughput Screening, Sep. 2007, 10(8):706-18.

Hall et al., Protein Microarray Technology., Mechanisms of Ageing and Development, Jan. 2007, 128(1):161-7.

Wu et al., Diagnostic devices as biomaterials: a review of nucleic acid and protein microarray surface performance issues., Journal of Biomaterials Science, Polymer Editions, Jan. 2008, 19(6):725-53.

Kricka and Master, Validation of Quality Control of Protein Microarray-based Analytical Methods., Molecular Biotechnology, Jan. 2008, 38(1):19-31.

Field et al., Accuracy and Reproducibility of Protein-DNA Microarray Technology., Analytics of Protein—DNA Interactions, Advances in Biochemical Engineering/Biotechnology, 2007, 104:87-110.

Foley et al., Surface impedance imaging technique., Analytical Chemistry, Jul. 2008, 80(13):5146-51.

Shan et al., Imaging Local Electrochemical Current via Surface Plasmon Resonance., Science, Mar. 2010, 327(5971):1363-6.

Wang et al., Electrochemical surface plasmon resonance: Basic formalism and experimental validation., Analytical Chemistry, Feb. 2010, 82(3):935-41.

Wang et al., Label-free imaging, detection, and mass measurement of single viruses by surface plasmon resonance., PNAS USA, Sep. 2010, 107(37):16028-32.

Wang et al., Single cells and intracellular processes studied by a plasmonic-based electrochemical impedance microscopy., Nature Chemistry, Mar. 2011, 3(3):249-55.

Shan et al., Plasmonic-based imaging of local square wave voltammetry., Analytical Chemistry, Oct. 2011, 83(19):7394-9.

Lu et al., Plasmonic-based electrochemical impedance spectroscopy: Application to molecular binding., Analytical Chemistry, Jan. 2012, 84(1):327-33.

Wang et al., Label-free measuring and mapping of binding kinetics of membrane proteins in single living cells., Nature Chemistry, Oct. 2012, 4(10):846-53.

Prime and Whitesides, Self-Assembled Organic Monolayers: Model Systems for Studying Adsorption of Proteins at Surfaces., Science, May 1991, 252(5009):1164-7.

Chang et al., Kinetic and Equilibrium Binding Characterization of Aptamers to Small Molecules using a Label-Free, Sensitive, and Scalable Platform., Analytical Chemistry, Apr. 2014, 86(7):3273-8.

De Mol et al., Kinetic analysis of the mass transport limited interaction between the tyrosine kinase lck SH2 domain and a phosphorylated peptide studied by a new cuvette-based surface plasmon resonance instrument., Analytical Biochemistry, Mar. 2000, 279(1):61-70.

Galopin et al., SPR biosensing coupled to a digital microfluidic microstreaming system., Biosensors and Bioelectronics, Dec. 2007, 23(5):746-50.

Edwards and Leatherbarrow, Determination of association rate constants by an optical biosensor using initial rate analysis., Analytical Biochemistry, Mar. 1997, 246(1):1-6.

Camillone, Diffusion-Limited Thiol Adsorption on the Gold(111) Surface., Langmuir, Feb. 2004, 20(4):1199-1206.

Schuck and Minton, Kinetic analysis of biosensor data: elementary tests for self-consistency., Trends in Biochemical Sciences, 1996, 21(12):458-60.

Schares et al., Three-dimensional modeling and simulation of DNA hybridization kinetics and mass transport as functions of temperature in a microfluidic channel., Electrophoresis, 2013, 34(14):2112-9.

Tao and Wang., Integrated Microarray Printing and Detection System., AzTE Disclosure.

* cited by examiner

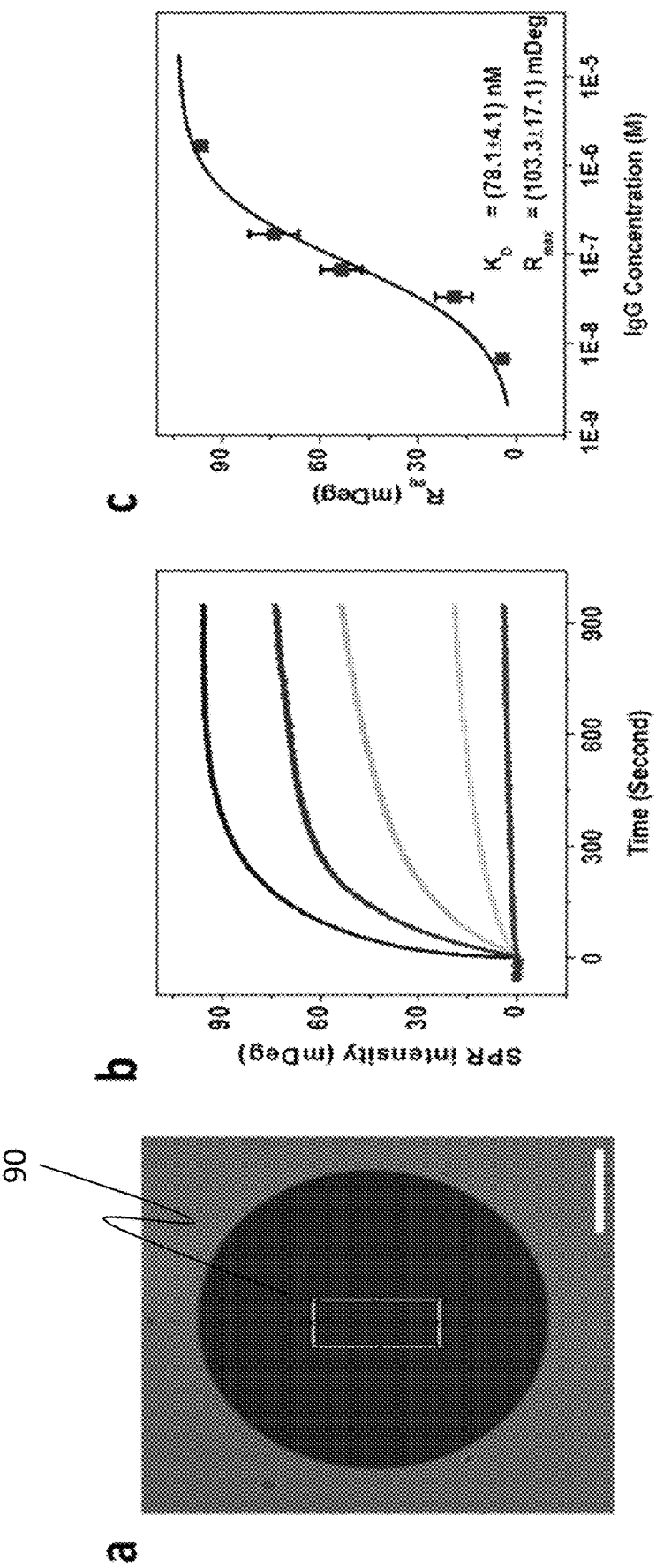

INTEGRATED MICROARRAY PRINTING AND DETECTION SYSTEM FOR MOLECULAR BINDING ANALYSIS

RELATED APPLICATION

This application claims priority from co-pending U.S. application No. 62/190,109 of Nongjian Tao et al., filed Jul. 8, 2015, entitled "INTEGRATED MICROARRAY PRINTING AND DETECTION SYSTEM FOR MOLECULAR BINDING ANALYSIS." U.S. application No. 62/190,109 is hereby incorporated by reference.

TECHNICAL FIELD

The present invention relates to microarray technology, and, more particularly, the invention relates to an integrated microarray printing and detection system (IMPDS) that enables high-throughput analysis of molecular interaction kinetics in microarray or whole-cell based formats.

BACKGROUND

Microarray technology has dramatically advanced the study of protein interactions leading to discovery and validation of new biomarkers and therapeutic drugs. Typically, protein microarrays are pre-spotted with target molecules in one device and then tested with probe molecules using another device. During each testing cycle, the entire microarray becomes exposed to the probe molecules. Though this approach has been shown to be effective for some applications, it inherently suffers from several key limitations that hinder it from gaining broader utility: 1) both the printing and analysis steps consume large sample volumes, which is particularly problematic where only small amounts of proteins are available or affordable; 2) the exposure of sample solution to the entire microarray restricts the kinetic interaction analysis of only one probe to N targets (1×N interactions only), significantly limiting the types of applications and analytical power of microarrays; and 3) complete microarrays must be pre-printed blindly with no feedback on spot uniformity, target activity, or probe selectivity which may lead to inconclusive data, unnecessary tests, and delays in obtaining effective results.

Proteins are the machines of life processes at the molecular level[1]. Typically, proteins carry out their functions through interactions with other proteins by creating complexes. Proteins must associate with each other to create these active complexes and then dissociate to stop the functional activity. Characterization of these complex interactions is fundamental to the understanding of life processes, making it essential to the discovery of cancer biomarkers, development of diagnostic assays, and screening for therapeutic drugs.

Conventional methods for detecting and characterizing protein-protein interactions either have low throughput or are limited to measuring steady-state, high-affinity protein interactions. They include end-point based methods such as co-immunoprecipitation (Co-IP), far western blots, various two-hybrid methods, and tandem affinity purification (TAP) prior to mass spectrometry. These methods provide little information about binding affinity and no information about the kinetics, however this information is crucial for a complete understanding of the dynamic proteome.

Surface plasmon resonance (SPR) has become an important technique for characterizing the protein interaction over the past decade, as it is a label-free method and provides substantial binding kinetics information.[2] However, most SPR systems require a flowing solution containing the analyte protein running over the target protein during the entire association phase. This process often lasts several minutes and even hours, which consumes a large amount of protein samples. The sample volume requirement often makes the measurement cost inhibitive, because preparation of protein samples usually involves multiple experimental steps (i.e. expression, extraction, and purification) and is labor intensive. This problem will be prominent for proteins that are difficult to express on the bacterial or to obtain in a general protocol. In addition, microfluidic based measurement has low throughput due to the limited the number of flow channels, and is also suffer from clotting of the fluidic channels by bubbles and impurities in the sample solution.

Microarrays are a high-throughput technology for screening of molecular interactions. Protein microarrays are widely used for quantifying interactions between proteins as well as interactions between proteins and macromolecules, which have vital importance to virtually every process in living cells[3-8]. However, the current approach has several well-known drawbacks[9-11], for example, both the printing and analysis steps consume large sample volumes, which is particularly problematic where only small amounts of proteins are available or affordable. Further, complete microarrays must be pre-printed blindly with no feedback on spot uniformity, target activity, or probe selectivity. This may lead to inconclusive data, unnecessary tests, and delays in obtaining effective results. Further yet, exposure of sample solution to the entire microarray restricts the interaction analysis of only one probe to N targets (1×N interactions only), significantly limiting the types of applications and analytical power of microarrays. Another problem with current techniques is that interaction analysis is typically limited to static or end-point evaluations such as concentration and affinity determination, providing little or limited information on binding kinetics.

The present invention overcomes the shortcomings in current microarray technology by presenting a novel integrated solution. An Integrated Microarray Printing and Detection System (IMPDS) for in-situ quantitative spotting with real-time measurement of drop-on-drop protein interactions is here disclosed for the first time. IMPDS features the ability to incorporate feedback of microarray formation and testing in order to generate more relevant results sooner, perform high resolution droplet-based testing with ultra-low nanoliter volume samples, conduct a more versatile M×N (many to many) protein kinetic interaction analysis of high-density microarrays, and measure molecular interactions and binding kinetics in cell-based assays.

BRIEF SUMMARY OF THE DISCLOSURE

This summary is provided to introduce, in a simplified form, a selection of concepts that are further described below in the Detailed Description. This summary is not intended to identify key features of the claimed subject matter, nor is it intended to be used as an aid in determining the scope of the claimed subject matter.

A method for analysis of molecular interaction kinetics in microarray or whole-cell based formats is disclosed where, in one aspect, a sensor chip is positioned on a transparent optical element, the sensor chip having a surface. The sensor chip surface is spotted with a plurality of target molecules to form a microarray. A movable printer head deposits a plurality of analyte droplets on the target molecules in the microarray. A light source is used to transmit light through the transparent optical element to excite surface plasmon resonance on the sensor chip surface. A detector receives reflected light transmitted through the transparent optical element from the sensor chip surface and signals from the detector are received. The received signals are processed into kinetic data to determine molecular interactions and binding kinetic properties for the plurality of analyte droplets.

In another aspect, an integrated microarray printing and detection system (IMPDS) for high-throughput analysis of protein interaction kinetics in microarray or whole-cell based formats is disclosed including a sensor chip having a surface, where the surface includes a plurality of molecular spots. A movable printing head is located over the surface. A light source is located to illuminate the sensor chip. A transparent optical element is positioned between the light source and the sensor chip so as to transmit light to the sensor chip surface. An imaging detector is located to receive the reflected light from a lens; and a processor is provided for signal processing of the image recorded with the imaging detector.

BRIEF DESCRIPTION OF THE DRAWINGS

While the novel features of the invention are set forth with particularity in the appended claims, the invention, both as to organization and content, will be better understood and appreciated, along with other objects and features thereof, from the following detailed description taken in conjunction with the drawings, in which:

FIG. 4A shows an SPR image of a droplet.

FIG. 4B graphically shows association curves for droplets with different concentration IgG binding to Anti-IgG; and the concentrations of IgG are 1667, 166.7, 66.7, 33.3 and 6.7 nM, respectively, from up to down.

FIG. 4C graphically shows equilibrium analysis of SPR intensity at steady state.

Figure 1A:
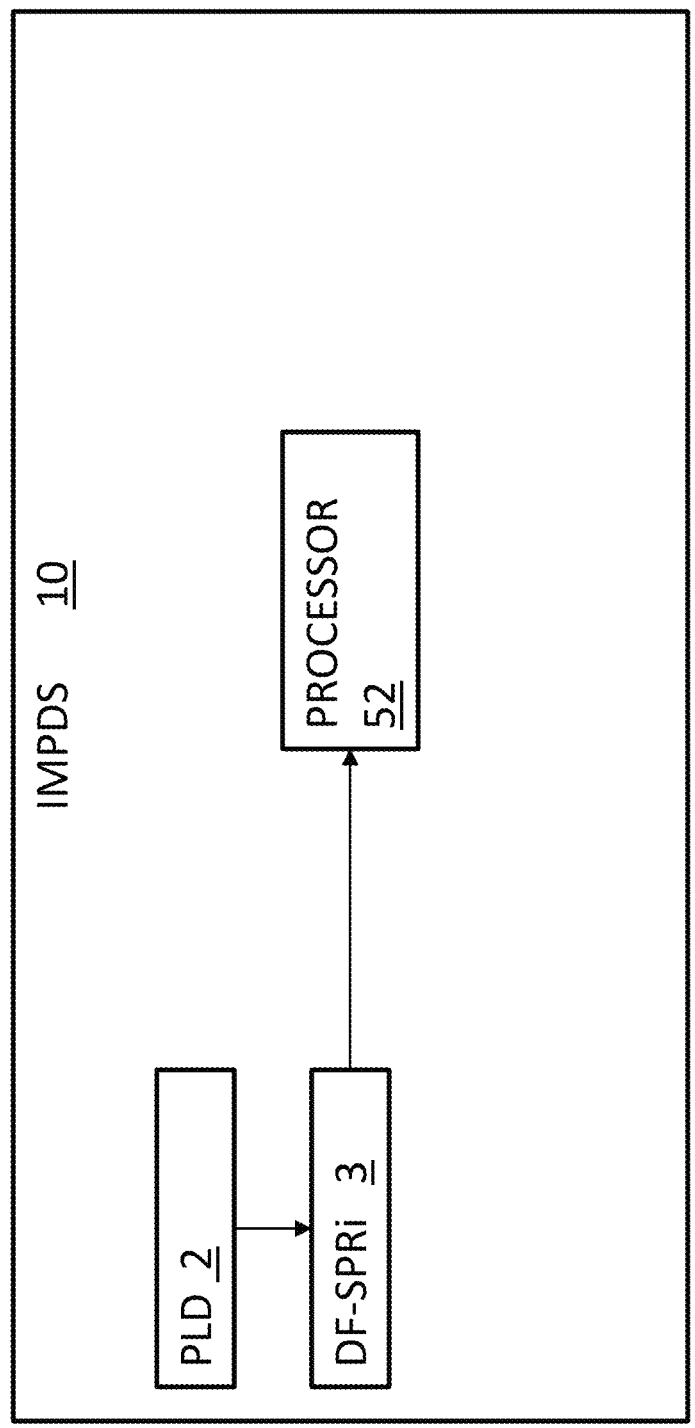
FIG. 1A shows a high level schematic illustrating an integrated microarray printing and detection system (IMPDS).

In the drawings, identical reference numbers identify similar elements or components. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

DETAILED DESCRIPTION

The following disclosure describes an integrated microarray printing and detection system (IMPDS). Several features of methods and systems in accordance with example embodiments are set forth and described in the figures. It will be appreciated that methods and systems in accordance with other example embodiments can include additional procedures or features different than those shown in the figures. Example embodiments are described herein with respect to an integrated microarray printing and detection system (IMPDS) that enables high-throughput analysis of protein interaction kinetics in microarray or whole-cell based formats. However, it will be understood that these examples are for the purpose of illustrating the principles, and that the invention is not so limited.

Unless the context requires otherwise, throughout the specification and claims which follow, the word "comprise" and variations thereof, such as, "comprises" and "comprising" are to be construed in an open, inclusive sense that is as "including, but not limited to."

Reference throughout this specification to "one example" or "an example embodiment," "one embodiment," "an embodiment" or combinations and/or variations of these terms means that a particular feature, structure or characteristic described in connection with the embodiment is included in at least one embodiment of the present disclosure. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Definitions

Generally, as used herein, the following terms have the following meanings when used within the context of microarray technology:

"1×PBS" refers to 1× Phosphate Buffered Saline.

"IMPDS" refers to integrated microarray printing and detection system.

The articles "a" or "an" and the phrase "at least one" as used herein refers to one or more.

As used herein, "plurality" is understood to mean more than one. For example, a plurality refers to at least two, three, four, five, ten, 25, 50, 75, 100, 1,000, 10,000 or more.

"SPR" as used herein refers to surface plasmon resonance technology.

"$k_a$" represents the equilibrium association rate constant.

"$k_d$" represents the equilibrium dissociation rate constant.

"$K_D$" represents the equilibrium dissociation constant, where $K_D=k_d/k_a$.

As used in this specification, the terms "processor" and "computer processor" encompass a personal computer, a tablet computer, a smart phone, a microcontroller, a microprocessor, a field programmable object array (FPOA), a digital signal processor (DSP), an application-specific integrated circuit (ASIC), a field programmable gate array (FPGA), a programmable logic array (PLA), or any other digital processing engine, device or equivalent capable of executing software code including related memory devices, transmission devices, pointing devices, input/output devices, displays and equivalents.

"Obtaining" is understood herein as manufacturing, purchasing, or otherwise coming into possession of.

Example Embodiments

In its most salient aspects, a novel method to measure protein interaction kinetics in a single droplet that reduces the sample volume requirement by 3-4 orders of magnitudes than conventional flow-based kinetic measurement is disclosed herein. A droplet with sub microliter or less volume in a humidity-controlled environmental chamber is replacing the microfluidic channels as the reactor for the protein interaction. The binding process in the droplet is measured by a SPRi setup. All kinetics constants of IgG/Anti-IgG interaction are obtained from the association will of the interaction at multiple concentrations of the analyte. The results are validated by conventional flowing-based measurements using the same setup. COMSOL simulation reveals that the smaller binding signal on the edge of the droplet is caused by mass transport limitation, and this limitation vanishes when the droplet volume approaching nanoliter scale. This droplet-based method also opens the door for high-throughput protein interaction study in a droplet-based microarray format. Both target and probing proteins can be delivered to the sensor surface via an integrated inkjet printer, and many to many interactions in a single microarray chip can be realized easily.

Referring now to FIG. 1A, a high level schematic diagram illustrating principles of an integrated microarray printing and detection system (IMPDS) is shown. The IMPDS 10 integrates multiple detection technologies into a single instrument including an ultra-low volume piezoelectric liquid dispensing (PLD) system 2 and a high-resolution distortion-free surface plasmon resonance imaging (DF-SPRi) system 3. The development of IMPDS not only streamlines and improves the performance of microarrays for high throughput analysis, but also enables new types of applications for proteomics research.

The novel approach disclosed herein overcomes the drawbacks of traditional microarray technologies with the following advantages:

(1) It produces higher-quality data with real-time evaluation and correction of spot uniformity and size during both target immobilization and probe testing.

(2) It surpasses end-point static observations with real-time quantification of interaction kinetics, enabling measurement of weak and transient interactions.

(3) It uses spot-on-spot nanodroplet-based interactions that consume much less sample volume and enable flexible M×N combinations of spot interactions.

(4) Real-time spot-on-spot analysis leads to more immediate opportunities for assay development and higher quality results sooner.

(5) It is compatible with cell-based microarray, enabling measurement of membrane protein interaction kinetics in their native cellular environment.

The disclosed methods and devices herein were designed to be capable of streamlining microarray spotting and detection into a single instrument for simpler, faster and more accurate results. The instant design should further promote ultra-low volume nanodroplet-based analysis of high-density microarrays. It will allow flexible and multiplexed M×N label-free protein interaction kinetic analysis in real time and analysis of cell-based microarrays with single cell resolution.

Figure 1B:
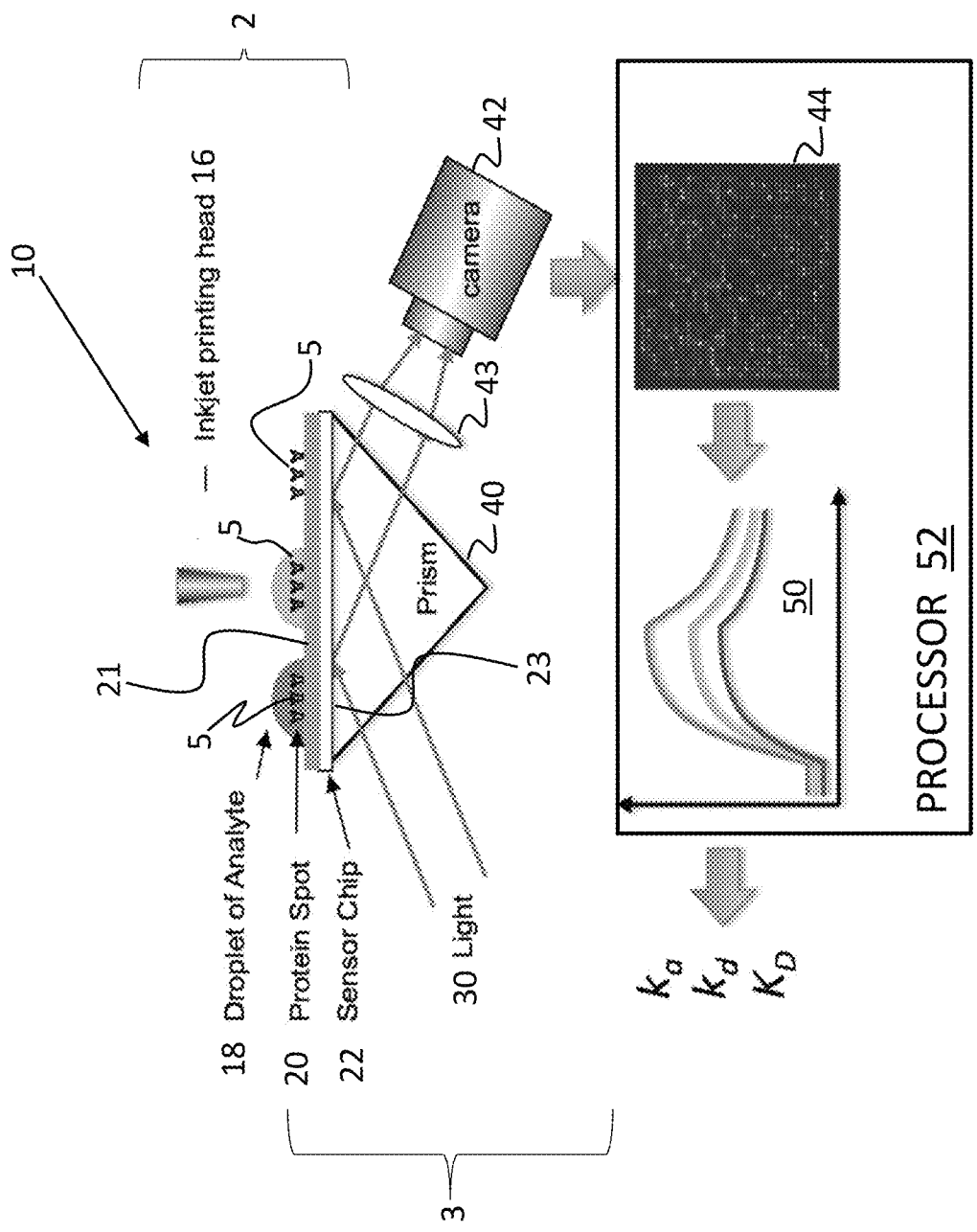
FIG. 1B shows a more detailed schematic illustrating principles of an integrated microarray printing and detection system (IMPDS).

Referring now to FIG. 1B, a more detailed schematic illustrating principles of an integrated microarray printing and detection system (IMPDS) is shown. An IMPDS 10 provides in-situ quantitative spotting with real-time measurement of protein interaction kinetics. In one example a sensor chip 22 has an upper surface 21 and a bottom surface 23. The sensor chip 22 may comprise a DNA microarray that is divided into a plurality of predetermined regions wherein protein spots 20 have been deposited so that the upper surface 21 includes a plurality of protein spots 20 deposited thereon. A movable printing head 16 is located over the upper surface 21 for the purpose of transporting and depositing droplets of analytes on the predetermined regions 5. Using a drop on a drop protocol differently sized droplets may be deposited in two phases, for example. A light source 30 is located to illuminate the sensor chip 22. A prism 40 is positioned between the light source 30 and the bottom surface 23 so as to transmit light to the bottom surface 23. The sensor chip 22 includes a plasmon resonance surface coating on the upper surface 21, such as gold or the like. In operation, the sensor chip 22 is activated by the light 30 and the kinetic activity is sensed by the imaging detector at the same time as target analyte data from the microarray.

A lens 43 is located to focus reflected light from the bottom surface to an imaging detector 42 located to receive the focused reflected light from the lens 43 to produce a microarray imaging data 44. A processor receives the microarray imaging data 44. Because the sensor chip includes a microarray combined with SPR surfaces, the processor includes a software program 50 or the like for signal processing of the microarray imaging data 44 combined with the kinetic data. For example the software program 50 may generate sensorgrams plotting image intensity vs. time profiles that provide quantitative kinetic information ($k_a$, $k_d$, and $K_D$) of an antibody binding to bacterial cells which may be introduced as droplets by the printing head.

In one example, the processor comprises a computer program held in memory for determining protein kinetic interaction analysis of high-density microarrays, while also measuring molecular interactions and binding kinetics in cell-based assays. The detector may be a camera, such as a CCD color imaging array or equivalents. The printing head may comprise an inkjet printing head which can be moved under control of a processor from samples to a plurality of positions on upper surface of the sensor chip.

Figure 2:
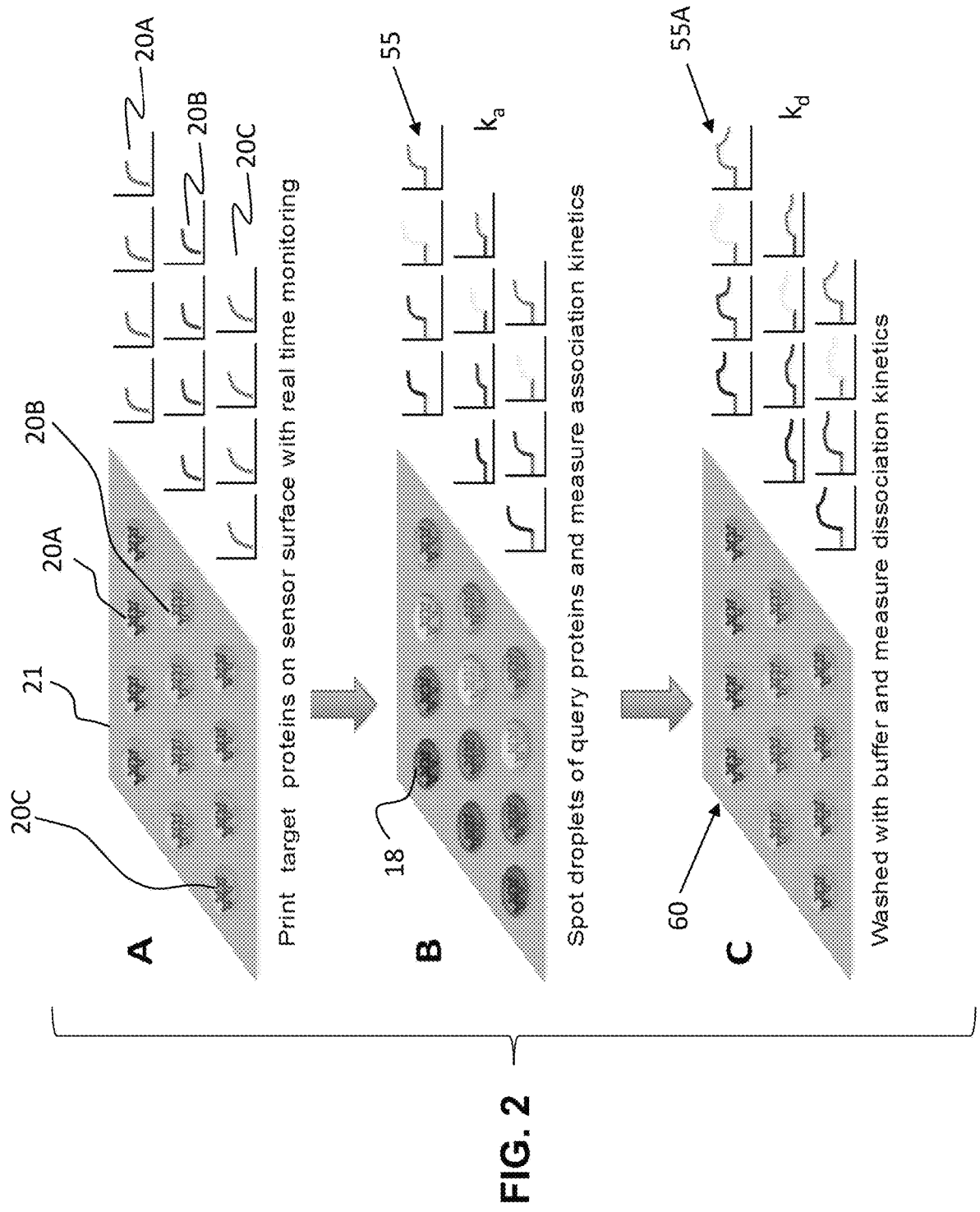
FIG. 2 illustrates workflow stages of an IMPDS showing in-situ microarray printing and droplet-based protein interaction kinetic analysis.

Referring now to FIG. 2, workflow stages of an IMPDS showing in-situ microarray printing and droplet-based protein interaction kinetic analysis are illustrated. At stage A, a sensor surface 21 pre-modified with attachment chemistry (such as activated HS-PEG-COOH or Streptavidin) is spotted with a plurality of target molecules 20A, 20B, and 20C. Since IMPDS actively monitors this process using the detector set up described hereinabove, it is uniquely able to monitor the time-dependent immobilization of target molecules, provide real-time correction of droplet chemistry or concentration, and touch up irregular or non-uniform spots. In this way, IMPDS can actively control and optimize the immobilization process, a key feature that is often overlooked when attempting to produce high-quality kinetic interaction data.

At stage B, after a global rinse of the substrate, nanodroplets 18 are spotted on top of pre-spotted target molecules 20A, 20B, and 20C. The IMPDS measures the time-dependent label-free binding interactions at each spot in real time. It is unique in its ability to perform droplet-based kinetic interaction analysis, utilizing its high-resolution detection, high-precision carriage, and ultra-low volume PLD. Droplet volumes of 10 nL for a first phase, Phase 1, and 1 nL for a second phase, Phase 2, saves significant sample volume (~4,000 times less than compared with conventional microarrays). Droplets are formed by rapid serial ejections (of about 24,000 cycles per second, for example) of 0.1 nL sub-droplets at a high velocity of several meters per second, thus helping to mix droplets that may be undergoing multi-step analysis.

Since each spot may contain a different type of probe molecule, M×N kinetic interactions can be measured on a single chip allowing multiplexed interaction analysis of microarrays. In this way, a single microarray chip may be used to study many complex interactions of various protein targets and probes, whereas numerous microarrays would be required for traditional microarray analysis. The IMPDS supports irregular spot patterns, such as in the case of analyzing a substrate of disordered cells allowing seek-and-spot capability for cell interaction analysis. The heterogeneity of cellular behavior makes cell analysis the perfect application for IMPDS. It is unique in its ability to measure protein interactions of cells and directly target specific cells for dosing/spotting[12-19].

At stage C, the query proteins are washed off with buffer, and the dissociation kinetics $k_d$ for all spots can be measured producing dissociation data on the tails of sensorgrams 55A. The main features of nanodroplet-based IMPDS and conventional microarray technology are compared and summarized in Table 1. The advantages of IMPDS over conventional microarrays are quite significant. IMPDS overcomes many of the technical limitations currently facing proteomics research and represents an innovative approach for drastically advancing this field.

TABLE 1

Major features comparison between droplets-based IMPDS and conventional microarray technology

| | IMPDS | Conventional Microarray |
|---|---|---|
| Pieces of equipment needed | 1 | At least 2, printer and reader |
| Real-time feedback of spot uniformity | Yes | No |
| Kinetic measurement | Yes | No |
| Weak and transient interaction | Detectable | Not detectable |
| Interaction throughput | Ultra-high, M × N | High, 1 × N |
| Sample volume | Down to 0.1 nL per spot | ~1 mL |
| Cell-based microarray | Yes | No |
| Concurrent multi-concentration measurement | Yes | No |
| Spot density | Up to 10,000 per chip | Up to 5,000 per chip |

Experimental Details:

The following materials were used in carrying out the experiments with the IMPDS. Phosphate-buffered saline (PBS, pH=7.4) was purchased from Thermo Fisher (Waltham, Mass.). DithiolalkanearomaticPEG3-OOH (Dithiol-PEG-OH) and dithiolalkanearomatic-PEG6-COOH (Dithiol-PEG-COOH) was purchased from SensoPath Technologies (Bozeman, Mont.). (See Supporting Information for the molecular structures). Sodium acetate (NaOAc), N-hydroxysuccinimide (NHS), N-ethyl-N'-(3-dimethylaminopropyl)carbodiimide hydrochloride (EDC), Immunoglobulin G (IgG) from human serum and anti-human IgG (Fab specific) antibody (anti-IgG) were obtained from Sigma-Aldrich (St. Louis, Mo.). Lyophilized IgG and Anti-IgG were dissolved in di-water as 10 mg/mL stock solution, and stored at −20° C. in 10 µL aliquots.

As discussed herein with respect to FIG. 1B, a prism-based SPRi setup was used in implementing the measurements discussed herein. In the setup, the sensor chip immobilized with Anti-IgG was placed on an equilateral SF-11 prism with a drop of BK7 index matching oil. A p-polarized light from a 670 nm light-emitting diode (LED, L7868-01, Hamamatsu, Japan) was directed through the prism onto the chip. The reflected beam produces the SPR image, which was captured by a CCD camera (Pike F032B, Allied Vision Technologies, Newburyport, Mass.) with a 12× variable zoom lens (Navitar Inc., Rochester, N.Y.). The LED was mounted on a temperature-controlled mounting socket and powered by a laser diode driver and a temperature controller (LDM 21, LDC201CU and TED2000, respectively, Thorlabs, Newton, N.J.).

Figures 3A, 3B:
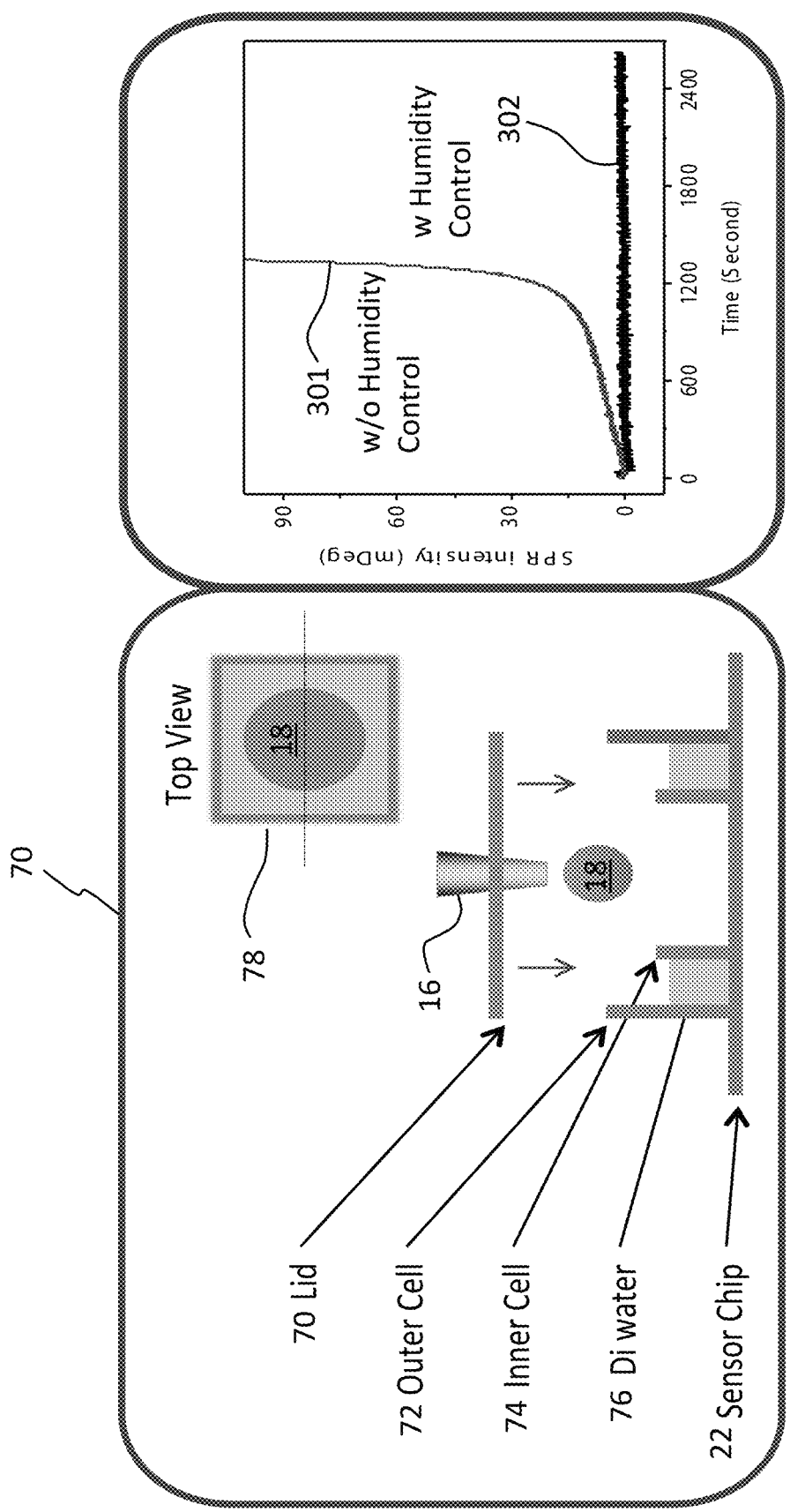
FIG. 3A shows a schematic illustration of a chamber for humidity control.
FIG. 3B shows SPR response for a droplet of PBS buffer with or without humidity control.

Referring now particularly to FIG. 3A, a schematic illustration of a chamber for humidity control is shown. A humidity control chamber 70 was designed to minimize droplet evaporation. The chamber 70 had double layers of PDMS cells 72, 74 and a PDMS Lid 76. The gap between the inner cell 74 and outer cell 72 was filled with deionized water 76 to increase the humidity level inside the chamber. After a droplet 18 was spotted on the sensor surface, the cell was sealed with the lid immediately to prevent sample evaporation. The sealed chamber eliminated the evaporation induced SPR signal drift (due to increase of bulk refractive index), (as shown in FIG. 3B). A 1 µL micro syringe with 0.02 µL precision was used to dispense the IgG droplet onto the sensor chip.

Referring briefly to FIG. 3B, curve 301 illustrates results without humidity control. Curve 302 shows improved results with humidity control.

In order to effect immobilization of Anti-IgG the SPR sensor chips used were BK-7 glass coverslip coated with 2 nm thick chromium layer covered by a 47 nm thick gold layer. Prior to the surface functionalization, the chips were rinsed by deionized water and ethanol, blown dry by nitrogen and cleaned by hydrogen flame. Next, the cleaned chips were incubated in 1 nM dithiol 50:1 PEG-OH/PEG-COOH ethanol solution overnight.[20] The mixed self-assembled monolayer (SAM) coated chips were washed by deionized water and ethanol, and blown dry by nitrogen before immobilizing the ligand protein. 0.5 ml freshly prepared deionized water solution containing 0.1 M NHS and 0.4 M EDC were deposited onto the chip surfaces to convert the —COOH group into active NHS ester receptors, which will react with the amino group of ligand protein to form an amide bond. After 20 minutes, the chip was thoroughly cleaned by deionized water, and then 10 μL of 20 μg/mL Anti-IgG dissolved in 20 mM NaOAc (pH=5.5) was immediately applied to the surface and kept for 1-1.5 hrs. to allow the protein bound to surface. Finally, the chip was cleaned by deionized water again.

To validate the kinetics parameters obtained from the droplet-based measurement, the binding kinetics of IgG to Anti-IgG were measured with a conventional SPRi flow-cell on the same setup. A gravity-based multi-channel drug perfusion system (SF-77B, Warner Instruments, CT) was used to control the local solution on the sensing area, with a flow rate of 350 μL/min.

Experimental Results:

Measuring the association of IgG to Anti-IgG in a droplet was carried out using an IMPDS as disclosed herein. The first challenge for droplet-based measurement is the evaporation of the droplet in the open air. Droplet evaporation not only increases the salt concentration in the droplets but also changes the temperature of the sensing area. Since SPR is sensitive to both salt concentration and temperature, evaporation causes significant signal drift and affects the accuracy of protein interaction measurement. Furthermore, the evaporation will eventually dry out the droplet, and terminate the binding reaction. Smaller droplets dry out faster. A 1 μl droplet typically dries out in minutes, which is not enough time to complete the kinetic measurement. To solve this problem, a humidity-controlled chamber was designed to minimize sample evaporation (See FIG. 3A). The droplet remains hydrated for over two hours in the chamber, sufficient to complete the kinetic measurement.

After solving the evaporation challenge, the binding experiment was conducted using a drop on a drop protocol (as illustrated in FIG. 1B). The ligand protein (Anti-IgG antibody) was immobilized onto the sensor chip prior to the experiment. The functionalized sensor chip was assembled onto the prism, and a droplet of 0.5 μL PBS was deposited onto the Anti-IgG functionalized area, in order to activate the surface and to measure the baseline. The SPR angle was tuned to near the resonance angle for the buffer, and the droplet was shown as a dark spot 78 on the chip (See FIG. 3A). After a stable baseline was recorded, the second droplet containing the analyte protein (IgG) was placed on top of the buffer droplet. The two droplets mixed together, and the association of IgG to the anti-IgG was measured. A control experiment shows that the mixed dithiol PEG-OH/PEG-COOH SAM effectively eliminated the non-specific adsorption of analyte protein (IgG), since no measurable analyte binding was found on a ligand free PEG surface.

Referring now to FIG. 4A, shows an SPR image of a droplet is shown. Experiments to extract the equilibrium disassociation constants were performed using the IMPDS described herein. The center area 90 of the droplet was used to obtain SPR responses as described below. Conventional kinetic measurements need both the association and dissociation phase of the binding data to obtain all kinetic constants. To simplify the liquid handling requirement for droplet-based interactions, the washing step was eliminated and all kinetic constants from the association curves were obtained at multiple analyte concentrations.

Referring now to FIG. 4B, association curves for droplets with different concentration IgG binding to Anti-IgG; and the concentrations of IgG are 1667, 166.7, 66.7, 33.3 and 6.7 nM, respectively, from up to down are shown. The SPR responses for different concentrations of analyte protein using averaged intensity in the center area 90 of the droplet (as shown in FIG. 4A). The dissociation constant can be obtained from the equilibrium SPR signal ($R_{eq}$) at steady state[21]. For a given concentration of analyte protein, $R_{eq}$ can be expressed as:

$$R_{eq} = \frac{c * R_{max}}{c + K_D} \quad (1)$$

Referring now to FIG. 4C equilibrium analysis of SPR intensity at steady state is graphically shown. Note that corrected concentrations were used here to extract the equilibrium dissociation constant. Here c is the concentration of the analyte protein, $R_{max}$ is the maximum SPR signal obtained when all surface binding sites are occupied, and $K_D$ is the equilibrium dissociation constant. However, the concentration of analyte protein in the droplet will decreased due to the depletion of binding reaction on the sensor surface. Thus, the analyte concentration must be corrected for the equilibrium analysis[22]. The equilibrium constant ($K_D$) was derived from the equilibrium SPR signal through equation (1) after correcting the analyte concentration, resulting in a $K_D$ value of 78.1±4.1 nM for the IgG/Anti-IgG interaction. Additionally, an $R_{max}$ value of 103.3±17.1 mDeg was also obtained simultaneously. However, $K_D$ is a static parameter describing the equilibrium state of the binding, and does not provide any kinetic information, which is quantified by association rate constant ($k_{on}$) and dissociation rate constant ($k_{off}$).

Figures 5A, 5B, 5C:
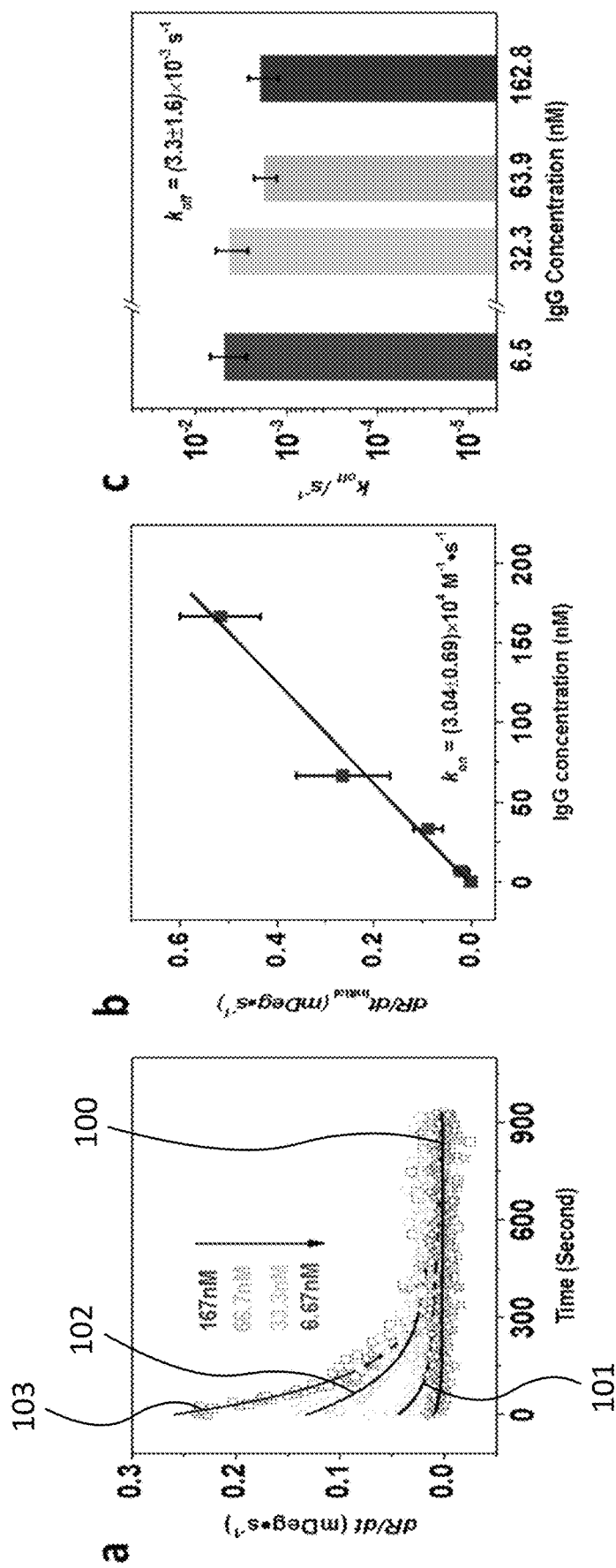
FIG. 5A graphically shows change of the binding rate vs. time for analyte protein in each concentration, which is generated from derivative of the SPR intensity data.
FIG. 5B graphically shows calculating the association rate constants from initial binding rates according to the equation of $dR/dt_{initial} = k_{on} * R_{max} * [A]_{bulk}$.
FIG. 5C graphically shows the dissociation rate constants obtained for each concentration according to $k_{off} = k_{on} * [A]_{free} * (R_{max} - R_{eq})/R_{eq}$.

Referring now to FIG. 5A, change of the binding rate vs. time for analyte protein in each concentration, which is generated from derivative of the SPR intensity data is graphically shown. As described herein, the association rate constant was calculated from initial binding rates using this data. The solid lines 100, 101, 102, and 103 were fitted using a polynomial to extract the initial binding rate (t→0), as well as visually guided.

For the binding reaction of analyte protein to its target in the droplet, the standard monovalent model of protein interaction will not justify the binding kinetics analysis[23], as the reduction of analyte concentration due to binding reaction and also the mass transport limitation will mislead the intrinsic kinetics analysis for the biomolecular interaction in the droplet. Thus, an initial rate analysis was adopted to extract the kinetics parameters of analyte to the target protein[24,25]. This method will not affected by the concentration change of analyte near the sensor surface, and also simplify the data processing work and requires fewer assumption on the equation form of the association curve.

Referring now to FIG. 5B, data used for calculating the association rate constants from initial binding rates is shown. For the binding reaction of free molecular to its immobilized target on the sensor chip, the initial interaction rate for a given analyte concentration can be expressed as equation (2):

$$\frac{dR_t}{dt}\bigg|_{t\to 0} = k_{on} * [A]_{bulk} * R_{max} \quad (2)$$

Where $k_{on}$ is the association rate constant of the binding reaction, $[A]_{bulk}$ is the initial concentration of analyte in the droplet, $R_{max}$ is as defined previously and already obtained above. The binding rates of analyte, IgG, in different concentrations to the sensor surface were first obtained by derivation of the time profile of association curves (as shown in FIG. 5A). A subsequent linearly plot of the initial rates against the analyte concentrations resulted in a $k_{on}$ value of $(3.04\pm0.69)\times10^4$ $M^{-1}s^{-1}$ as determined according to the slope of this straight line and the maximum SPR intensity obtained above.

Referring now to FIG. 5C, data used for calculating the dissociation rate constants obtained for each concentration is shown. When the binding reaction reaches steady state, the association rate is equal to the dissociation rate, that is, equation (3) is established:

$$k_{off} = k_{on} * [A]_{free} * (R_{max} - R_{eq})/R_{eq} \quad (3)$$

Where $k_{off}$ is the dissociation rate constant, $[A]_{free}$ is the analyte concentration after association. And $k_{on}$, $R_{max}$ and $R_{eq}$ are defined as above. Thus, the value of $k_{off}$ can be further calculated by equation (3). The average value of $(3.3\pm1.6)\times10^{-3}$ $s^{-1}$ was determined according to the one calculated from each concentration. Then, and a $K_D$ value of $(108.5\pm58.1)$ nM were obtained by $K_D = k_d/k_a$. This value is closely match to $K_D$ calculated from the equilibrium analysis describe in last paragraph, suggesting this fitting model is valid for our case (26). Additional details of the derivations are provided in the Supporting Information.

Figure 6:
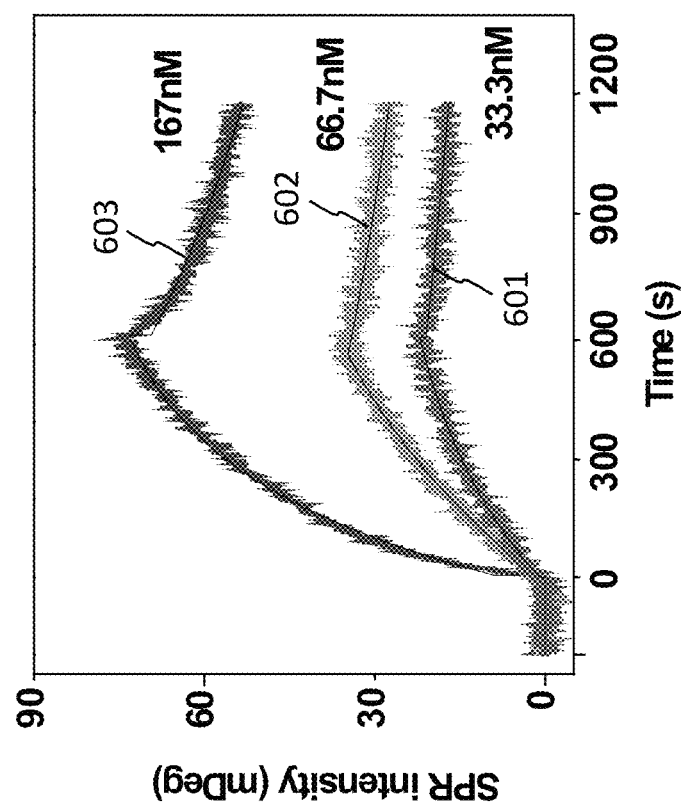
FIG. 6 graphically shows conventional SPR kinetic measurement results.

Referring now to FIG. 6, conventional SPR kinetic measurement results are graphically shown. Sensorgrams 601, 602, 603 were generated using the IMPDS for different concentrations of IgG binding to Anti-IgG immobilized on the sensor surface. The values of $(3.1\pm1.0)\times104$ M-1·s-1, $(1.1\pm0.3)\times10-3$ s-1, and $(34.3\pm6.2)$ nM for $k_a$, $k_d$, $K_D$, respectively, were obtained according a 1:1 model of protein interaction (the solid line was the fitting result for each concentration). The flowing rate of IgG solution was 350 μL/min, and the IgG concentrations were 167, 66.7 and 33.3 nM as marked in the figure, respectively.

To validate the droplet based kinetic measurement results, the IgG/Anti-IgG binding kinetics using the conventional fluidic method on the same SPR setup, and with both association and dissociation phases were also measured. The kinetics parameters were calculated by global fitting of all sensorgrams based on a monovalent model for protein interaction. The binding kinetics obtained from the conventional flow-through and those from the droplet-based method are similar as listed in Table 1. The small differences in the rate constants are due to the bulk analyte concentration change in the droplet, and will be discussed in next section.

The consumption of analyte protein in the droplet-based method is reduced about 500 folds to 0.29 μg compared to that in the conventional SPR system. The amount of ligand protein needed for the droplet-based method can also be reduced to similar level when the ligand immobilization is also using a droplet-based approach, which can be realized by integrate the SPR system with an inkjet printer.

Edge Effect in the Droplet-Based Reaction

Figure 7A:
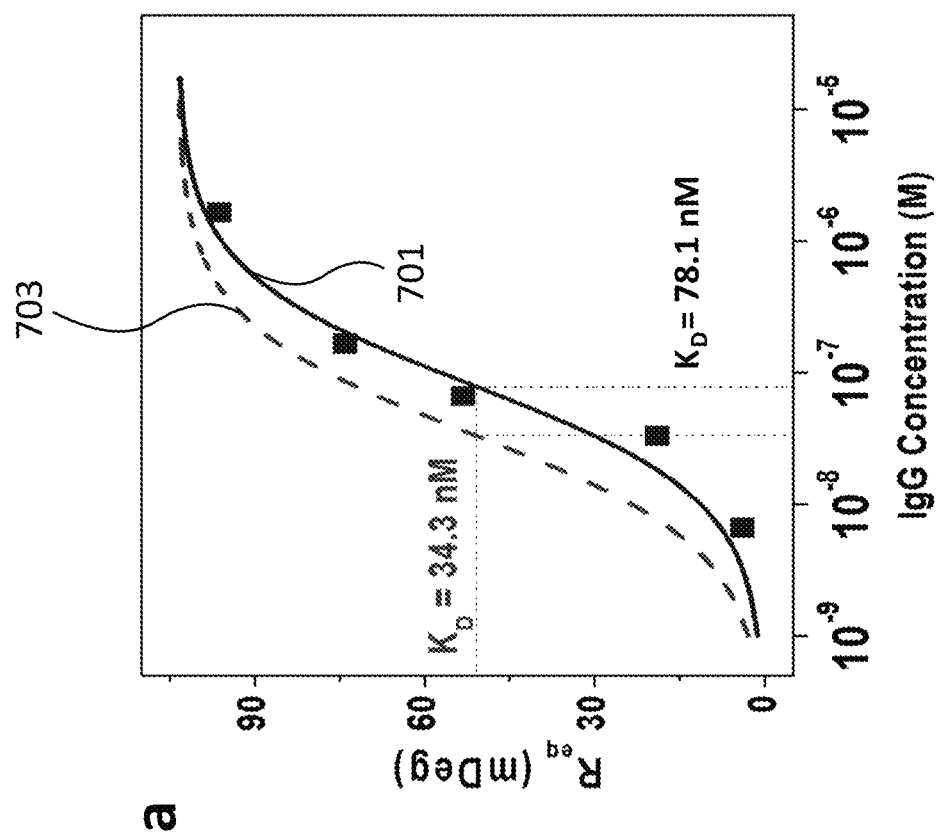
FIG. 7A graphically shows overestimation of the analyte concentration near the sensor surface caused a higher determination of equilibrium dissociation constant, $K_D$.

Referring now to FIG. 7A, there illustrated is how overestimation of the analyte concentration near the sensor surface caused a higher determination of equilibrium dissociation constant, $K_D$. As shown in Table 2 below, the droplet-based approach displayed an almost same association rate constant, $k_{on}$, as the conventional fluidic system, but a slight higher $k_{off}$ and $K_D$. It is believed that this effect is due to the overestimation of free analyte concentration after the association near the sensor surface, $[A]_{free}$. For a certain SPR intensity at equilibrium state, the estimated IgG concentrations near the sensor surface as represented by curve 701 used for kinetics analysis are a bit higher than the "actual" ones suggested by conventional fluidic system represented by curve 703. This hypothesis is suggested by the observation that the binding rate within the droplet becomes location-dependent as the analyte concentration drops.

Figure 7D:
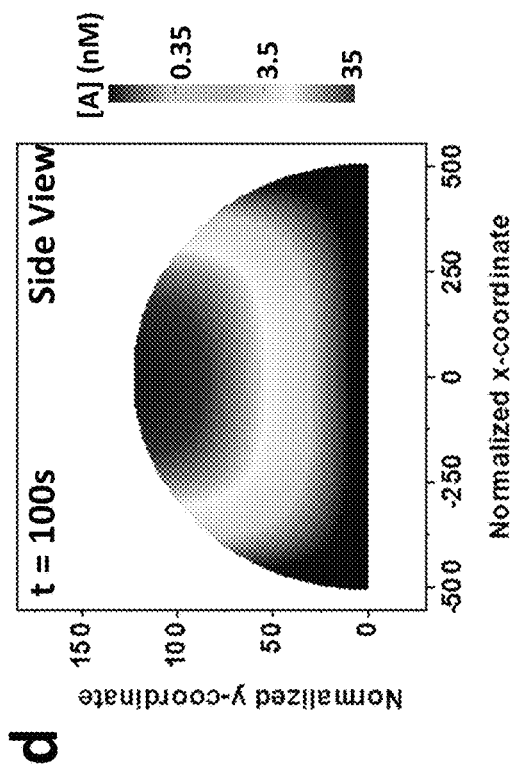
FIG. 7D illustrates concentration distribution of analyte protein in the droplet after association of 100 s.
Figure 7E:
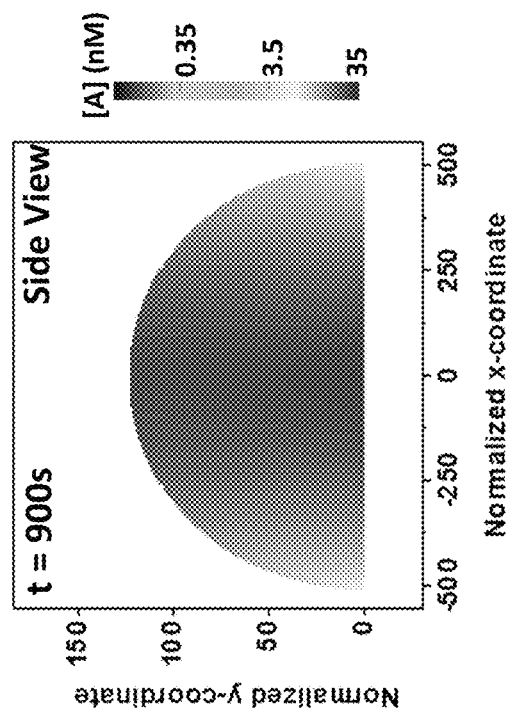
FIG. 7E illustrates concentration distribution of analyte protein in the droplet after association of 900 s.
Figure 7B:
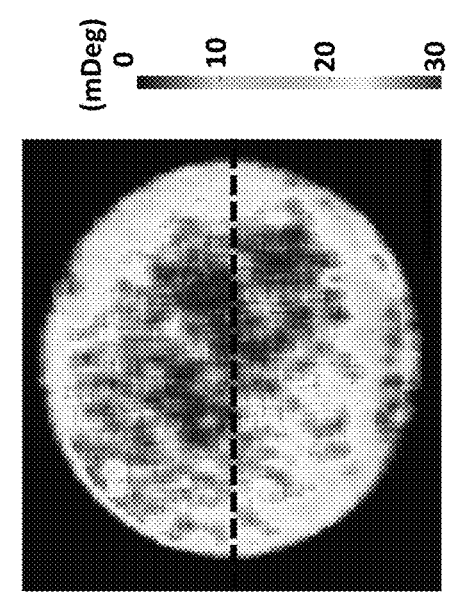
FIG. 7B illustrates binding intensity distribution for IgG in the droplet at the concentration of 33.3 nM after the association of 900 s. Scale bar: 500 μm.

Referring now to FIG. 7B, binding intensity distribution for IgG in the droplet at the concentration of 33.3 nM after the association of 900 s on a scale bar of 500 μm is shown in a heat map format.

Figure 7C:
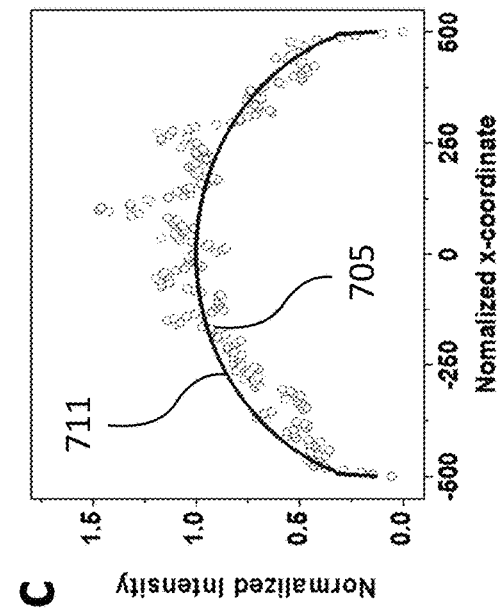
FIG. 7C illustrates SPR intensity along the central lines, and the red circles are the raw data points and the blue line is the simulation result by a COMSOL program.

Referring now to FIG. 7C, SPR intensity along the central lines, and the circles are the raw data points and the solid line 711 is the simulation result by a COMSOL program is illustrated. The intensity is normalized by the one in the central point where x=0. (Also as shown in circles 705, the center of the droplet generates a higher IgG binding signal than the edge. To understand the location-dependent phenomenon, a two-dimensional model was developed using commercially available software from COMSOL Multiphysics to simulate the change of IgG concentration in the droplet during the binding process. The model includes two modules: transport of diluted species and surface reactions. The former is to simulate the diffusion of IgG molecules in the droplet, and the latter is to simulate the IgG/Anti-IgG binding reaction on the sensor surface. These two parts were coupled by the following equation: (27)

$$\frac{\partial c}{\partial t} + \nabla \cdot (-D\nabla c) = k_{on} * c * ([B] - c_s) - k_{off} * c_s \quad (4)$$

Where c is the concentration of IgG for the binding reaction, which changes over time. D is the diffusion coefficient of IgG in the media, [B] is the concentration of Anti-IgG immobilized on the sensor surface, and $c_s$ is the surface concentration of IgG indicating the amount of IgG associated to Anti-IgG. And t, $k_{on}$ and $k_{off}$ were defined previously.

Through this model, the concentration gradient of IgG in the droplet and on the sensing surface was simulated. The results revealed that the location dependent variation of binding response is caused by a mass transport-limited binding kinetics, which depends on the diffusion rate of probe molecules and the shape and size of the droplet. When the binding rate is faster than the diffusion rate, probe molecules at the edge will deplete faster than those at the center, resulting in a weaker binding response at the droplet edge (as represented by solid line 711).

TABLE 2

Comparison of the binding kinetics obtained by conventional and droplet-based SPR

|  | Conventional SPR | Droplet-based SPR |
| --- | --- | --- |
| $k_a$ ($10^4$ $M^{-3}s^{-1}$) | 3.1 ± 1.0 | 3.0 ± 0.7 |
| $k_d$ ($10^{-3}s^{-1}$) | 1.1 ± 0.3 | 2.3 ± 0.6 |
| $K_D$ (nM) | 34.3 ± 6.2 | 108.5 ± 58.1 (78.1 ± 4.1)* |
| Sample consumption (μg) | 140 | 0.29 |

*The value in the bracket is calculated from equilibrium analysis.

Referring now to FIG. 7D, concentration distribution of analyte protein in the droplet after association of 100 s is illustrated. For the 33.3 nM IgG droplet, after association of 100 s, the concentration of IgG near the sensor surface was almost depleted, especially the edge. However, the binding rate on the center, where approaching equilibrium at first, will decrease due to the reduction of surface concentration of immobilized anti-IgG, [B].

FIG. 7E illustrates concentration distribution of analyte protein in the droplet after association of 900 s. Then, more analyte molecules will diffuse to the edge area and the concentration variation in the droplet will gradually become smaller. After association of 900 s, the binding signal on the center area has already reached the maximum intensity and can be used to estimate the equilibrium state of binding reaction in the droplet, thus the center areas of the droplets were analyzed in the preliminary data. However, the concentration difference still exists in the droplet even at 900 s. When the concentrations of free analyte, $[A]_{free}$, used for the kinetics analysis is higher than the actual ones near the sensor surface, the overestimation on $k_{off}$ and/or $K_D$ will be caused.

Figure 8A:
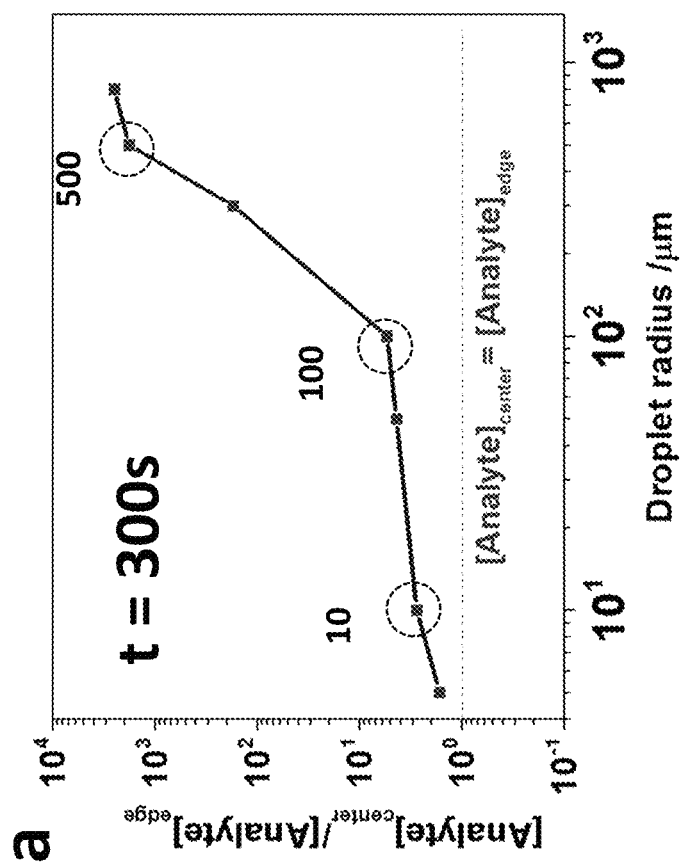
FIG. 8A graphically shows Dependence of [Analyte] center/[Analyte] edge on the droplet size after association of 300 s.
Figures 8B, 8C:
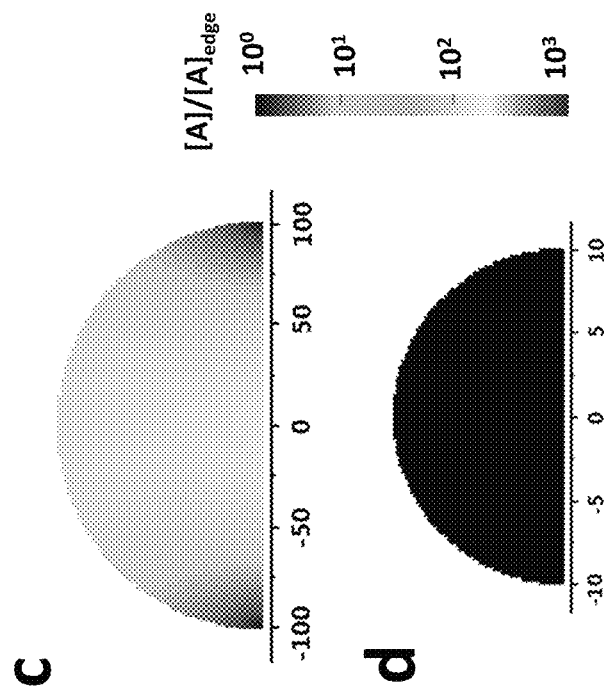
FIG. 8B-FIG. 8D indicate the distribution of concentration variation in the droplet with a radius of 500 μm, 100 μm, 10 μm, respectively.
Figure 8D:
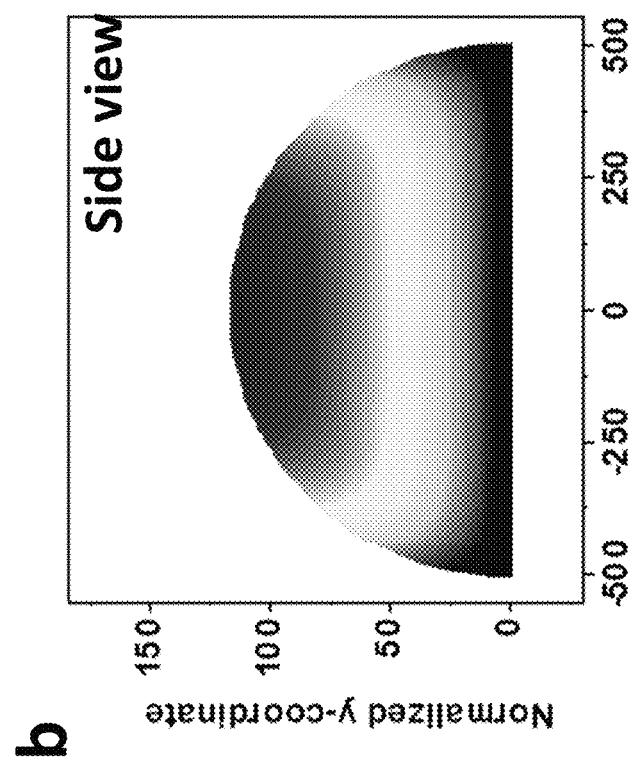

Referring now to FIG. 8A, dependence of [Analyte] center/[Analyte] edge on the droplet size after association of 300 s is graphically shown. [Analyte] center/[Analyte]edge, represented on the abscissa or x-axis, is the ratio of analyte concentration at the top center to that at the edge, indicating the largest concentration variation in the droplet. The ordinate, or y-axis, is a measure of the droplet radius in micrometers. FIG. 8B-FIG. 8D indicate the distribution of concentration variation in the droplet with a radius of 500 µm, 100 µm, 10 µm, respectively. In FIG. 8B-FIG. 8D, the ordinate represents the normalized Y-coordinate and the abscissa is the normalized capital X-coordinate/µm. In FIG. 8B normalized Y-coordinate ranges from about 0 to about 150 in the normalized X-coordinate ranges from about −502 to about +500. In FIG. 8C the normalized capital X-coordinate/ µm ranges from about −100 to about +100. In FIG. 8D the normalized capital X-coordinate/µm ranges from about −10 to about +10.

The invention has been described herein in considerable detail in order to comply with the Patent Statutes and to provide those skilled in the art with the information needed to apply the novel principles of the present invention, and to construct and use such exemplary and specialized components as are required. However, it is to be understood that the invention may be carried out by different equipment, and devices, and that various modifications, both as to the equipment details and operating procedures, may be accomplished without departing from the true spirit and scope of the present invention.

REFERENCES

The teachings of the following publications are incorporated herein in their entirety by this reference.
1. Tyson J J, Chen K C, Novak B. Sniffers, buzzers, toggles and blinkers: dynamics of regulatory and signaling pathways in the cell. Current opinion in cell biology. 2003; 15(2):221-31. PubMed PMID: 12648679.
2. Homola J. Surface plasmon resonance sensors for detection of chemical and biological species. Chem Rev. 2008; 108(2):462-93. doi: 10.1021/cr068107d. PubMed PMID: WOS:000253165500007.
3. Zhu H, Cox E, Qian J. Functional protein microarray as molecular decathlete: a versatile player in clinical proteomics. Proteomics Clinical applications. 2012; 6(11-12):548-62. doi: 10.1002/prca.201200041. PubMed PMID: 23027439; PMCID: 3600421.
4. Hu S, Xie Z, Qian J, Blackshaw S, Zhu H. Functional protein microarray technology. Wiley interdisciplinary reviews Systems biology and medicine. 2011; 3(3):255-68. doi: 10.1002/wsbm.118. PubMed PMID: 20872749; PMCID: 3044218.
5. Zhao J, Patwa T H, Lubman D M, Simeone D M. Protein biomarkers in cancer: natural glycoprotein microarray approaches. Current opinion in molecular therapeutics. 2008; 10(6):602-10. PubMed PMID: 19051138; PMCID: 2920894.
6. Hober S, Uhlen M. Human protein atlas and the use of microarray technologies. Current opinion in biotechnology. 2008; 19(1):30-5. doi: 10.1016/j.copbio.2007.11.006. PubMed PMID: 18187316.
7. Tao S C, Chen C S, Zhu H. Applications of protein microarray technology. Combinatorial chemistry & high throughput screening. 2007; 10(8):706-18. PubMed PMID: 18045082.
8. Hall D A, Ptacek J, Snyder M. Protein microarray technology. Mechanisms of ageing and development. 2007; 128(1):161-7. doi: 10.1016/j.mad.2006.11.021. PubMed PMID: 17126887; PMCID: 1828913.
9. Wu P, Castner D G, Grainger D W. Diagnostic devices as biomaterials: a review of nucleic acid and protein microarray surface performance issues. Journal of biomaterials science Polymer edition. 2008; 19(6):725-53. doi: 10.1163/156856208784522092. PubMed PMID: 18534094.
10. Kricka L J, Master S R. Validation and quality control of protein microarray-based analytical methods. Molecular biotechnology. 2008; 38(1):19-31. doi: 10.1007/s12033-007-0066-5. PubMed PMID: 18095188.
11. Field S, Udalova I, Ragoussis J. Accuracy and reproducibility of protein-DNA microarray technology. Advances in biochemical engineering/biotechnology. 2007; 104:87-110. PubMed PMID: 17290820.
12. Foley K J, Shan X, Tao N J. Surface impedance imaging technique. Anal Chem. 2008; 80(13):5146-51. doi: Doi 10.1021/Ac800361p. PubMed PMID: ISI: 000257270600051.
13. Shan X, Patel U, Wang S, Iglesias R, Tao N. Imaging local electrochemical current via surface plasmon resonance. Science. 2010; 327(5971):1363-6. Epub 2010 Mar. 13. doi: 327/5971/1363 [pii]10.1126/science.1186476. PubMed PMID: 20223983.
14. Wang S P, Huang X P, Shan X N, Foley K J, Tao N J. Electrochemical Surface Plasmon Resonance: Basic Formalism and Experimental Validation. Anal Chem. 2010; 82(3):935-41. doi: Doi 10.1021/Ac902178f. PubMed PMID: ISI000273983700027.
15. Wang S, Shan X, Patel U, Huang X, Lu J, Li J, Tao N. Label-free imaging, detection, and mass measurement of single viruses by surface plasmon resonance. Proc Natl Acad Sci USA. 2010; 107(37):16028-32. Epub 2010 Aug. 28. doi: 1005264107 [pii]10.1073/pnas.1005264107. PubMed PMID: 20798340; PMCID: 2941305.
16. Wang W, Foley K, Shan X, Wang S P, Eaton S, Nagaraj V J, Wiktor P, Patel U, Tao N J. Single cells and intracellular processes studied by a plasmonic-based electrochemical impedance microscopy. Nature Chemistry. 2011; 3(3):249-55. doi: Doi 10.1038/Nchem.961. PubMed PMID: ISI:000287525600018.
17. Shan X, Wang S, Wang W, Tao N. Plasmonic-based imaging of local square wave voltammetry. Anal Chem. 2011; 83(19):7394-9. Epub 2011 Jul. 29. doi: 10.1021/ac201392r. PubMed PMID: 21793508; PMCID: 3288114.
18. Lu J, Wang W, Wang S, Shan X, Li J, Tao N. Plasmonic-based electrochemical impedance spectroscopy: applica- 18. ...tion to molecular binding. Anal Chem. 2012; 84(1):327-33. Epub 2011 Nov. 30. doi: 10.1021/ac202634h. PubMed PMID: 22122514; PMCID: 3299414.
19. Wang W, Yang Y, Wang S, Nagaraj V J, Liu Q, Wu J, Tao N. Label-free measuring and mapping of binding kinetics of membrane proteins in single living cells. Nature chemistry. 2012; 4(10):846-53. Epub 2012 Sep. 25. doi: 10.1038/nchem.1434. PubMed PMID: 23000999.
20. Prime K L, Whitesides G M. SELF-ASSEMBLED ORGANIC MONOLAYERS—MODEL SYSTEMS FOR STUDYING ADSORPTION OF PROTEINS AT SURFACES. Science. 1991; 252(5009):1164-7. doi: 10.1126/science.252.5009.1164. PubMed PMID: WOS:A1991FN05600048.
21. Chang A L, McKeague M, Liang J C, Smoke C D. Kinetic and Equilibrium Binding Characterization of Aptamers to Small Molecules using a Label-Free, Sensitive, and Scalable Platform. Anal Chem. 2014; 86(7): 3273-8. doi: 10.1021/ac5001527. PubMed PMID: WOS: 000333776600006.
22. de Mol N J, Plomp E, Fischer M J E, Ruijtenbeek R. Kinetic analysis of the mass transport limited interaction between the tyrosine kinase Ick SH2 domain and a phosphorylated peptide studied by a new cuvette-based surface plasmon resonance instrument. Anal Biochem. 2000; 279(1):61-70. doi: 10.1006/abio.1999.4464. PubMed PMID: WOS:000085775200008.
23. Galopin E, Beaugeois M, Pinchemel B, Camart J C, Ouazaoui M B, Thomy V. SPR biosensing coupled to a digital microfluidic microstreaming system. Biosens Bioelectron. 2007; 23(5):746-50. doi: 10.1016/j.bios.2007.08.009. PubMed PMID: WOS: 000251754400023.
24. Edwards P R, Leatherbarrow R J. Determination of association rate constants by an optical biosensor using initial rate analysis. Anal Biochem. 1997; 246(1):1-6. doi: 10.1006/abio.1996.9922. PubMed PMID: WOS: A1997WL81800001.
25. Camillone N. Diffusion-limited thiol adsorption on the gold(111) surface. Langmuir. 2004; 20(4):1199-206. doi: 10.1021/la030121n. PubMed PMID: WOS: 000189013400031.
26. Schuck P, Minton A P. Kinetic analysis of biosensor data: Elementary tests for self consistency. Trends BiochemSci. 1996; 21(12):458-60. doi: 10.1016/s0968-0004(96) 20025-8. PubMed PMID: WOS:A1996VZ80500002.
27. Schares E S, Edwards T L, Moorman M W, Polsky R, Brozik S M, Manginell R P. Three-dimensional modeling and simulation of DNA hybridization kinetics and mass transport as functions of temperature in a microfluidic channel. Electrophoresis. 2013; 34(14):2112-9. doi: 10.1002/elps.201200692. PubMed PMID: WOS: 000327662400021.

What is claimed is:

1. An integrated microarray printing and detection system (IMPDS) for high-throughput analysis of protein interaction kinetics in microarray or whole-cell based formats comprising:
a prism;
a sensor chip, placed on the prism, the sensor chip having an upper surface and a bottom surface;
a gold plasmon resonance surface on the upper surface of the sensor chip;
a light source configured to illuminate the sensor chip through the prism whereby the sensor chip is activated by the light source;
a lens located to focus reflected light from the bottom surface of the sensor chip;
a camera located to receive the reflected light, where the camera is configured to produce microarray imaging data from the reflected light;
an inkjet printing head located over the sensor chip;
a processor connected to and programmed to control the camera and the inkjet printing head;
where the processor is further programmed to control the inkjet printing head to deposit a plurality of target molecule droplets on a plurality of predetermined regions on the sensor chip in a first phase and then individually deposit a plurality of analyte droplets on the plurality of target molecule droplets in a second phase, wherein the plurality of target molecule droplets and the plurality of analyte droplets each have a radius of less than 500 µm; and
wherein the processor is further programmed to provide quantitative data also generate quantitative kinetic information from the microarray imagine data produced by the camera.

2. The system of claim 1 wherein the gold plasmon resonance surface of the sensor chip is pre-modified with attachment chemistry comprising activated streptavidin or thiol carboxylic PEG.

3. The system of claim 1 wherein the light source is positioned to illuminate the sensor chip at the surface plasmon resonance angle.

4. The system of claim 1 wherein the processor is further programmed to generate sensorgrams plotting image intensity vs. time profiles that provide quantitative kinetic information of an analyte binding to bacterial cells which may be introduced as droplets by the printing head.

* * * * *